United States Patent [19]

Behr et al.

[11] Patent Number: 5,318,674
[45] Date of Patent: Jun. 7, 1994

[54] PROCESS FOR PREPARING PERFLUOROALKANESULFONYL FLUORIDES

[75] Inventors: Fredrick E. Behr; Yuri Cheburkov, both of Woodbury; John C. Hansen, Lakeland, all of Minn.

[73] Assignee: Minnesota Mining and Manufacturing Company, St. Paul, Minn.

[21] Appl. No.: 85,540

[22] Filed: Jun. 30, 1993

[51] Int. Cl.$^5$ ............................ C25B 1/24; C25B 3/08
[52] U.S. Cl. ...................................... 204/59 F; 204/72; 562/825
[58] Field of Search ................. 204/59 F, 72, 82, 94; 562/825

[56] References Cited

U.S. PATENT DOCUMENTS

| | | | |
|---|---|---|---|
| 2,519,983 | 8/1950 | Simons | 204/62 |
| 2,713,593 | 7/1955 | Brice et al. | 260/535 |
| 2,732,398 | 1/1956 | Brice et al. | 260/503 |
| 2,852,554 | 9/1958 | England | 260/481 |
| 3,028,321 | 4/1962 | Danielson et al. | 204/59 |
| 3,250,808 | 5/1966 | Moore et al. | 260/535 |
| 3,692,643 | 9/1972 | Holland | 204/59 R |
| 4,332,954 | 6/1982 | Koshar | 549/10 |
| 4,425,199 | 1/1984 | Hamada et al. | 204/59 F |
| 4,739,103 | 4/1988 | Hansen et al. | 560/125 |
| 4,962,282 | 10/1990 | Marraccini et al. | 562/825 |

OTHER PUBLICATIONS

England, D. C., et al., J. Am. Chem. Soc., 82, 6181–88 (1960).
Howells, R. D. and J. D. McCown, Chem. Rev., 77, 69 (1977).
Kirk-Othmer *Encyclopedia of Chemical Technology*, Fourth Edition, vol. 3, p. 1017, John Wiley & Sons, New York, (1992).
Knunyants, I. L. and G. A. Sokolski, Angew. Chem. Int. Ed. Engl., 11, 583–85 (1972).
Mohtasham,J. and G. L. Gard, Coord. Chem. Reviews 112, 49–55 (1992).
Novikova, M. et al., J. Fluorine Chem., 58, 326 (1992).
Simons, J. H. (Editor), *Fluorine Chemistry*, vol. 1, pp. 416–418 (1950), Academic Press, Inc.
Stang, P. J. and M. R. White, Aldrichimica Acta, 16, 15 (1983).
Volkov, N. D. et al., Synthesis, 972 (1979).

*Primary Examiner*—John Niebling
*Assistant Examiner*—Edna Wong
*Attorney, Agent, or Firm*—Gary L. Griswold; Walter N. Kirn; Lucy C. Weiss

[57] ABSTRACT

A process for preparing perfluoroalkanesulfonyl fluorides, e.g., perfluoromethanesulfonyl fluoride, comprises electrochemically fluorinating in the presence of anhydrous hydrogen fluoride at least one precursor compound selected from the group consisting of $\alpha,\beta$-difluoroalkane-$\beta$-sultones, e.g., 1,1,2,2-tetrafluoroethane sultone, and the corresponding $\alpha$-halocarbonylfluoroalkanesulfonyl halides, e.g., fluorocarbonyldifluoromethanesulfonyl fluoride. The process can be used to prepare perfluoroalkanesulfonyl fluorides in good yield and can be, for example, both more electrically-efficient and more fluorine-efficient than the conventional preparative method involving the electrochemical fluorination of hydrocarbon alkanesulfonyl halides.

13 Claims, No Drawings

PROCESS FOR PREPARING PERFLUOROALKANESULFONYL FLUORIDES

This invention relates to a process for preparing perfluoroalkanesulfonyl fluorides.

Perfluoroalkanesulfonyl fluorides are useful as starting materials for the preparation of a variety of useful compounds. For example, perfluoromethanesulfonyl fluoride can be used to prepare perfluoromethanesulfonic acid, which has been reported to be the strongest of all known monoprotic organic acids. (See R. D. Howells and J. D. McCown, Chem. Rev., 77, 69 (1977).) Perfluoroalkanesulfonyl fluorides can also be utilized to prepare perfluoroalkanesulfonamides (which are useful as herbicides, antimicrobials, and antiobesity drugs) and salts such as lithium perfluoroalkanesulfonates and lithium bis(perfluoroalkanesulfonyl)imides (which are useful as electrolyte salts for battery applications). (See P. J. Stang and M. R. White, Aldrichimica Acta, 16, 15 (1983) and Kirk-Othmer *Encyclopedia of Chemical Technology*, Fourth Edition, Volume 3, page 1017, John Wiley & Sons, New York, (1992).)

Perfluoroalkanesulfonyl fluorides have been prepared from a variety of different starting materials by such methods as electrochemical fluorination, direct fluorination, and photolysis.

For example, U.S. Pat. No. 2,732,398 (Brice et al.) discloses the preparation of perfluoroalkanesulfonyl fluorides by the electrochemical fluorination (ECF) in anhydrous liquid hydrogen fluoride of the corresponding hydrocarbon alkanesulfonyl halides.

J. Fluorine Chem., 58, 326 (1992) (M. Novikova et al.) describes the preparation of perfluoromethanesulfonyl fluoride by direct gas-phase fluorination of (fluorosulfonyl)difluoroacetyl fluoride.

Synthesis, 972 (1979) (N. D. Volkov et al.) discloses the preparation of halodifluoromethanesulfonyl fluorides by photolysis of the corresponding 2-halo-2-oxodifluoroethanesulfonyl fluorides.

Both hydrocarbon and halocarbon sultones have been fluorinated (directly or electrochemically) to provide various types of fluorinated compounds other than perfluoroalkanesulfonyl fluorides.

For example, U.S. Pat. No. 4,332,954 (Koshar) discloses the electrochemical fluorination of a hydrocarbon sultone, 1,3-propanesultone, to provide 3-(fluorosulfonyl)perfluoropropanoyl fluoride (see Example 2).

U.S. Pat. No. 4,425,199 (Hamada et al.) describes the electrochemical fluorination of hydrocarbon sultones, e.g., 1,3-propanesultone, or partially-halogenated hydrocarbon sultones to provide (ω-fluorosulfonyl)-haloaliphatic carboxylic acid fluorides, e.g., 3-(fluorosulfonyl)perfluoropropionic acid fluoride. This patent also describes the electrochemical fluorination of 3-(fluorosulfonyl)perfluoropropionic acid fluoride to provide perfluoroethanesulfonyl fluoride (see the "Reference Example" in column 9).

U.S. Pat. No. 4,962,282 (Marraccini et al.) discloses the direct fluorination of halocarbon β-sultones in the presence of a fluorination catalyst (preferably an alkali metal fluoride supported on a metal material) to provide the corresponding fluorooxy-fluorosulfonyl-fluorocompounds.

Briefly, this invention provides a process for preparing perfluoroalkanesulfonyl fluorides comprising electrochemically fluorinating in the presence of anhydrous hydrogen fluoride at least one precursor compound selected from the group consisting of α,β-difluoroalkane-β-sultones, e.g., 1,1,2,2-tetrafluoroethane sultone, and the corresponding α-halocarbonylfluoroalkanesulfonyl halides, e.g., fluorocarbonyldifluoromethanesulfonyl fluoride. Preferably, an α,β-difluoroalkane-β-sultone or a mixture of an α,β-difluoroalkane-β-sultone and the corresponding α-halocarbonylfluoroalkanesulfonyl halide is utilized in the process. Most preferably, an α,β-difluoroalkane-β-sultone is utilized.

The process of the invention provides a route to perfluoroalkanesulfonyl fluorides which can be both more electrically-efficient and more fluorine-efficient than the conventional route involving the electrochemical fluorination of hydrocarbon alkanesulfonyl halides. The process also generally avoids the production of hazardous by-products, such as the hydrogen chloride gas and chlorine gas which can result from the electrochemical fluorination of hydrocarbon alkanesulfonyl chlorides. Rather, the by-product of the process is carbonyl fluoride ($COF_2$), which is useful, e.g., in preparing fluorocarbon ether acid fluorides (see U.S. Pat. No. 3,250,808 (Moore et al.)). The process of the invention also produces less by-product hydrogen gas than the conventional route, allowing for easier collection of the desired product. The process provides perfluoroalkanesulfonyl fluorides in good yield by the electrochemical fluorination of fluorocarbon β-sultone precursors which can be easily prepared in one step from readily available industrial starting materials.

A class of α,β-difluoroalkane-β-sultones which can be utilized as precursor compounds in the process of this invention is that whose members fall within the following representational general formula:

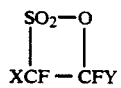

wherein X is selected from the group consisting of hydrogen; fluorine; chlorine; pentafluorosulfanyl; fluoroalkyl and fluoro(alkoxyalkyl) groups having from 1 to about 20 carbon atoms, containing no more than one atom of hydrogen or chlorine for every two carbon atoms, optionally containing carbon-carbon unsaturation, optionally being pentafluorosulfanyl-substituted, and optionally containing catenary nitrogen, oxygen, or sulfur; perfluoroalkyl and perfluoro(alkoxyalkyl) groups having from 1 to about 20 carbon atoms, optionally containing carbon-carbon unsaturation, optionally being pentafluorosulfanyl-substituted, and optionally containing catenary nitrogen, oxygen, or sulfur; and alkyl groups having from 1 to about 12 carbon atoms; and Y is selected from the group consisting of chlorine and fluorine. Preferably, the fluoroalkyl, fluoro(alkoxyalkyl), perfluoroalkyl, and perfluoro(alkoxyalkyl) groups have from 1 to about 12 carbon atoms, most preferably, from 1 to about 7 carbon atoms.

A preferred subclass of α,β-difluoroalkane-β-sultones which can be utilized as precursor compounds in the process of this invention is that whose members fall within said representational general formula:

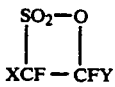

wherein X is selected from the group consisting of fluorine, chlorine, and perfluoromethyl; and Y is selected from the group consisting of fluorine and chlorine. These compounds are inexpensive and readily available.

α,β-difluoroalkane-β-sultones can be prepared by the reaction of monomeric sulfur trioxide with fluoroolefins, as described by D. C. England et al. in *J. Am. Chem. Soc.*, 82, 6181–88 (1960), by J. Mohtasham and G. L. Gard in Coord. Chem. Reviews 112, 49–55 (1992), and by I. L. Knunyants and G. A. Sokolski in Angew. Chem. Int. Ed. Engl. 11, 583–85 (1972), which descriptions are incorporated herein by reference. (See also U.S. Pat. No. 2,852,554 (England).)

A class of α-halocarbonylfluoroalkanesulfonyl halides which can be utilized as precursor compounds in the process of this invention is that whose members fall within the following representational general formula:

wherein X is selected from the group consisting of hydrogen; fluorine; chlorine; pentafluorosulfanyl; fluoroalkyl and fluoro(alkoxyalkyl) groups having from 1 to about 20 carbon atoms, containing no more than one atom of hydrogen or chlorine for every two carbon atoms, optionally containing carbon-carbon unsaturation, optionally being pentafluorosulfanyl-substituted, and optionally containing catenary nitrogen, oxygen, or sulfur; perfluoroalkyl and perfluoro(alkoxyalkyl) groups having from 1 to about 20 carbon atoms, optionally containing carbon-carbon unsaturation, optionally being pentafluorosulfanyl-substituted, and optionally containing catenary nitrogen, oxygen, or sulfur; and alkyl groups having from 1 to about 12 carbon atoms; and Y and Y' are selected from the group consisting of chlorine and fluorine, with the proviso that at least one of the groups Y and Y' is fluorine. Preferably, the fluoroalkyl, fluoro(alkoxyalkyl), perfluoroalkyl, and perfluoro(alkoxyalkyl) groups have from 1 to about 12 carbon atoms, most preferably, from 1 to about 7 carbon atoms.

A preferred subclass of α-halocarbonylfluoroalkanesulfonyl halides which can be utilized as precursor compounds in the process of this invention is that whose members fall within said representational general formula:

wherein X is selected from the group consisting of fluorine, chlorine, and perfluoromethyl; and Y and Y' are selected from the group consisting of fluorine and chlorine, with the proviso that at least one of the groups Y and Y' is fluorine.

α-Halocarbonylfluoroalkanesulfonyl halides result from the base-catalyzed isomerization of α,β-difluoroalkane-β-sultones, as described by England et al., supra, pages 6181–82, and by Mohtasham and Gard, supra, pages 56–57, which descriptions are incorporated herein by reference.

The electrochemical fluorination of the above-described precursor compounds can be carried out by introducing, e.g., by pumping, at least one precursor compound to a Simons electrochemical fluorination cell containing anhydrous hydrogen fluoride (or to which anhydrous hydrogen fluoride is simultaneously or subsequently added). The Simons electrochemical fluorination cell is an electrolytic cell in which is suspended an electrode pack comprising a series of alternating and closely-spaced cathode plates (typically made of iron or nickel or nickel alloy) and anode plates (typically made of nickel). The cell body can be made of, for example, carbon steel and is usually provided with a cooling jacket, a valved outlet pipe at the bottom through which can be drained the settled liquid cell product ("drainings"), a valved inlet pipe at the top of the cell for charging the cell with the precursor compound(s) and liquid anhydrous hydrogen fluoride, and an outlet pipe at the top of the cell for removing gaseous cell products evolved in operation of the cell. The outlet pipe can be connected to a refrigerated condenser for condensing hydrogen fluoride vapors and relatively hydrogen fluoride-insoluble fluorochemical products. The resulting condensed materials can be phase-separated, the fluorochemical products collected, and the hydrogen fluoride returned to the cell. U.S. Pat. No. 2,519,983 contains a drawing of such a Simons electrolytic cell and its appurtenances, and a description and photographs of laboratory and pilot plant cells appear at pages 416–18 of Volume 1 of *Fluorine Chemistry*, edited by J. H. Simons, published in 1950 by Academic Press, Inc., New York.

The Simons cell can be operated at average applied direct current cell voltages in the range of from about 4 to about 8 volts (sufficiently high, but not so high as to generate free fluorine), at current densities of from about 20 to about 300 amps/m$^2$ of active anode surface, at substantially atmospheric or ambient pressure or higher, and at temperatures ranging from below about 0° C. to about 20° C. or as high as about 50° C. (so long as the electrolytic solution remains liquid). The initial amount of precursor compound(s) in the anhydrous hydrogen fluoride can be, for example, from about 5 to about 20 weight percent, and both the precursor compound(s) and the anhydrous hydrogen fluoride can be replenished from time to time. If desired, a conventional conductivity additive, such as sodium fluoride, acetic anhydride, or an organic sulfur-containing compound such as that described in U.S. Pat. Nos. 3,028,321 (Danielson), 3,692,643 (Holland), and 4,739,103 (Hansen), can be added to the cell to increase the conductivity of the cell contents. The amount of said additive can be, for example, from about 1 to about 20 percent by weight (based upon the weight of the precursor compound(s)).

Other details of the Simons electrochemical fluorination process and cell will be omitted here in the interest of brevity, and the disclosures of such technology in the above-cited references to such technology can be referred to for such detail, which disclosures are incorporated herein by reference.

The process of the invention can be carried out continuously (by continuously introducing precursor compound(s) to the cell and continuously withdrawing liquid cell product), semi-continuously (by continuously introducing precursor and intermittently withdrawing product, or by intermittently introducing precursor and continuously withdrawing product), or batchwise. The continuous mode of operation is preferred for large-scale operation, as it enables better control of the operating variables. The desired perfluoroalkanesulfonyl fluoride product is preferably recovered, for example, by condensation followed by phase-separation into an upper hydrogen fluoride-containing phase and a lower fluorochemical-containing phase (e.g., by use of a decanter) and subsequent draining of the lower phase. The drainings can be further purified, if desired, by passage through a column containing sodium fluoride in order to remove any residual hydrogen fluoride. In addition, low temperature distillation can be used to isolate the desired fluorochemical products.

The process of the invention provides a route to perfluoroalkanesulfonyl fluorides which can be both more electrically-efficient and more fluorine-efficient than the conventional route involving the electrochemical fluorination of hydrocarbon alkanesulfonyl halides. The process provides perfluoroalkanesulfonyl fluorides in good yield by the electrochemical fluorination of fluorocarbon $\beta$-sultone precursors which can be easily prepared in one step from readily available industrial starting materials. The perfluoroalkanesulfonyl fluoride products of the process are useful as starting materials for the preparation of a variety of compounds having utility, for example, as strong acids, herbicides, antimicrobials, antiobesity drugs, and as electrolyte salts for battery applications.

This invention is further illustrated by the following examples, but the particular materials and amounts thereof recited in these examples, as well as other conditions and details, should not be construed to unduly limit this invention.

EXAMPLES

EXAMPLE 1

Preparation of Perfluoromethanesulfonyl Fluoride by the Electrochemical Fluorination of 1,1,2,2-Tetrafluoroethane Sultone Into an electrochemical fluorination cell (Simons cell), which was of the type described in U.S. Pat. No. 2,713,593 (Brice et al.) and which contained anhydrous liquid hydrogen fluoride, was fed 296 g of distilled 1,1,2,2-tetrafluoroethane sultone (prepared by the method described on pages 6183–84 of England et al., supra) in a semi-continuous manner over a period of 24.3 hours, while electrolyzing the resulting hydrogen fluoride solution using an average voltage of 6.3 volts at a current density of 277 amps/m$^2$ (25.7 amps/ft$^2$) at 33° C. and at a pressure of 0.055 MPa (8 psig). The gaseous products from the cell were passed through a −40° C. condenser, whereby most of the liquefied hydrogen fluoride was returned to the cell. The low-boiling, gaseous fluorochemical products of the electrochemical fluorination reaction were passed through a column containing sodium fluoride pellets to remove residual hydrogen fluoride, and the resulting purified products were subsequently collected in liquid nitrogen-cooled traps. Analysis of the purified products by gas chromatography (GC)/Fourier Transform Infrared (FTIR) (weight percent) showed the presence of CF$_3$SO$_2$F (45%), COF$_2$ (45%), CF$_4$ (2%), SO$_2$F$_2$ (3%), and some unidentified materials (5%).

EXAMPLE 2

Preparation of Perfluoromethanesulfonyl Fluoride by the Electrochemical Fluorination of a Mixture of 1,1,2,2-Tetrafluoroethane Sultone and Fluorocarbonyldifluoromethanesulfonyl Fluoride Employing essentially the procedure described in Example 1, a mixture containing 5.7 g of 1,1,2,2-tetrafluoroethane sultone (prepared as in Example 1) and 3.8 g of the isomeric fluorocarbonyldifluoromethanesulfonyl fluoride (resulting from isomerization of the 1,1,2,2-tetrafluoroethane sultone upon prolonged storage under ambient conditions) was fed to the cell in a semi-continuous manner over a 4.6 hour period while electrolyzing the resulting hydrogen fluoride solution using an average of 6.0 volts at a current density of 162 amps/m$^2$ (15.0 amps/ft$^2$) at 20° C. and at atmospheric pressure. The gaseous cell products were passed through a −40° C. condenser, whereby most of the liquefied hydrogen fluoride was returned to the cell. The low-boiling, gaseous fluorochemical products from the condenser were passed through a column containing sodium fluoride pellets to remove residual hydrogen fluoride, and the resulting purified products were subsequently collected in liquid nitrogen-cooled traps. Analysis of the purified products by GC/FTIR (weight percent) showed the presence of CF$_3$SO$_2$F (31%), COF$_2$ (39%), CF$_4$ (19%), SO$_2$F$_2$ (4%), and small amounts of other cleavage products (7%).

EXAMPLE 3

Preparation of Perfluoroethanesulfonyl Fluoride by the Electrochemical Fluorination of 1-(Trifluoromethyl)-1,2,2-trifluoroethane Sultone Employing essentially the procedure described in Example 1, 40.0 g of 1-(trifluoromethyl)-1,2,2-trifluoroethane sultone (which can be prepared by the method described in England et al., supra, page 6184) was fed to the cell in a batch type manner over a 22.7 hour period, while electrolyzing the resulting hydrogen fluoride solution using an average voltage of 6.7 volts at a current density of 21.6 amps/m$^2$ (2.0 amps/ft$^2$) at 20° C. and at atmospheric pressure. The gaseous products from the cell were passed through a −40° C. condenser, whereby most of the hydrogen fluoride was returned to the cell. The low-boiling fluorochemical products of the electrochemical fluorination reaction were passed through a column containing sodium fluoride pellets to remove residual hydrogen fluoride, and the resulting purified products were subsequently collected in liquid nitrogen-cooled traps. Analysis of the purified products by GC/FTIR (weight percent) showed the presence of C$_2$F$_5$SO$_2$F, (39%), COF$_2$ (53%), and a mixture (8%) of CF$_4$, SO$_2$F$_2$, C$_3$F$_8$, CF$_2$=CFCF$_3$ and unidentified materials.

EXAMPLE 4

Preparation of Perfluoromethanesulfonyl Fluoride by the Electrochemical Fluorination of a Mixture of 2-Chloro-1,1,2-trifluoroethane Sultone and 1-Chloro-1,2,2-trifluoroethane Sultone Employing essentially the procedure described in Example 1, 20.7 g of an isomeric mixture of 2-chloro-1,1,2-trifluoroethane sultone and 1-chloro-1,2,2-trifluoroethane sultone (which can be prepared by the method described in England et al., supra, page 6186)

was fed to the cell in a semi-continuous manner over a 46.5 hour period, while electrolyzing the resulting hydrogen fluoride solution using an average voltage of 6.4 volts at a current density of 53.9 amps/m$^2$ (5.0 amps/ft$^2$) at 30° C. and at a pressure of 0.041 MPa (6 psig). The gaseous products from the cell were passed through a −40° C. condenser, whereby most of the hydrogen fluoride was liquefied and returned to the cell. The low-boiling fluorochemical products of the electrochemical fluorination reaction were passed through a column containing sodium fluoride pellets to remove residual hydrogen fluoride, and the resulting purified products were subsequently collected in liquid nitrogen-cooled traps. Analysis of the purified products by GC/FTIR (weight percent) showed the presence of CF$_3$SO$_2$F (30%), COF$_2$ (27%), SO$_2$F$_2$ (18%), CF$_4$ (10%), C$_2$F$_6$ (5%), CF$_3$COF (4%), SOF$_4$ (3%), and very low levels (3%) of other unidentified materials. Only small amounts of Cl$_2$ and HCl were qualitatively identified in the cell by-product gases.

EXAMPLE 5

Preparation of Perfluorobutanesulfonyl Fluoride by the Electrochemical Fluorination of 1-(Perfluoro-n-propyl)-1,2,2-trifluoroethane Sultone 1-(Perfluoro-n-propyl)-1,2,2-trifluoroethane sultone precursor cell feed was prepared by the following procedure. Sulfur trioxide (6.49 g, freshly distilled from 65% oleum) and perfluoro-1-pentene (21.18 g) were placed in a flame-dried (to exclude adventitious moisture), thick-walled Pyrex TM brand glass ampoule, and the ampoule was sealed using a flame torch. The ampoule (which contained a two-phase heterogeneous mixture) was placed in a steam bath and was heated for 16 hours. During the heating time the two-phase mixture became homogeneous and remained homogeneous after completion of the reaction and subsequent cooling. The contents of the ampoule was then transferred to a distillation flask. Upon distillation, two fractions were obtained: Fraction A (1 g, boiling point 26°–28° C.) and Fraction B (15 g, boiling point 80°–83° C). Fraction A was identified by FTIR analysis to be unreacted perfluoroolefinic starting material. Fraction B, a fuming liquid, was analyzed by GC/MS (gas chromatography/mass spectrometry) and $^{19}$F NMR (Nuclear Magnetic Resonance Spectroscopy), which showed the fraction to be greater than 95% 1-(perfluoro-n-propyl)-1,2,2-trifluoroethane sultone.

Employing essentially the procedure described in Example 1, 13.8 g of 1-(perfluoro-n-propyl)-1,2,2-trifluoroethane sultone was fed to the cell in a semi-continuous manner over a 23.4 hour period, while electrolyzing the resulting hydrogen fluoride solution using an average voltage of 7.0 volts at a current density of 32.3 amps/m$^2$ (3.0 amps/ft$^2$) at ambient temperature and at atmospheric pressure. The fluorochemical products and by-products from the cell were passed through a −40° C. condenser, whereby most of the hydrogen fluoride and higher boiling fluorochemical products condensed and formed two phases; the hydrogen fluoride (upper) phase was returned to the cell. GC/FTIR analysis of the 6.9 g of liquid fluorochemical products condensed by the −40° C. condenser showed C$_4$F$_9$SO$_2$F as the major product component. The non-condensing (i.e., lower-boiling) fluorochemical by-products of the electrochemical fluorination reaction were passed through a column containing sodium fluoride pellets to remove residual hydrogen fluoride, and the resulting purified by-products were subsequently collected in liquid nitrogen-cooled traps. Analysis of the purified by-products by GC/FTIR showed the presence of COF$_2$, CF$_4$, SO$_2$F$_2$, C$_4$F$_{10}$, CF$_3$SO$_2$F, and C$_3$F$_8$, along with minor amounts of other unidentified products.

Various modifications and alterations of this invention will become apparent to those skilled in the art without departing from the scope and spirit of this invention.

We claim:

1. A process for preparing perfluoroalkanesulfonyl fluorides comprising electrochemically fluorinating in the presence of anhydrous hydrogen fluoride at least one precursor compound selected from the group consisting of α,β-difluoroalkane-β-sultones and the corresponding α-halocarbonylfluoroalkanesulfonyl halides.

2. The process of claim 1 wherein said at least one precursor compound is selected from the group consisting of α,β-difluoroalkane-β-sultones and mixtures of an α,β-difluoroalkane-β-sultone and the corresponding α-halocarbonylfluoroalkanesulfonyl halide.

3. The process of claim 2 wherein said compound is an α,β-difluoroalkane-β-sultone.

4. The process of claim 1 wherein said α,β-difluoroalkane-β-sultones are selected from the class whose members fall within the representational general formula

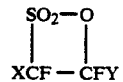

wherein X is selected from the group consisting of hydrogen; fluorine; chlorine; pentafluorosulfanyl; fluoroalkyl and fluoro(alkoxyalkyl) groups having from 1 to about 20 carbon atoms, containing no more than one atom of hydrogen or chlorine for every two carbon atoms, optionally containing carbon-carbon unsaturation, optionally being pentafluorosulfanyl-substituted, and optionally containing catenary nitrogen, oxygen, or sulfur; perfluoroalkyl and perfluoro(alkoxyalkyl) groups having from 1 to about 20 carbon atoms, optionally containing carbon-carbon unsaturation, optionally being pentafluorosulfanyl-substituted, and optionally containing catenary nitrogen, oxygen, or sulfur; and alkyl groups having from 1 to about 12 carbon atoms; and Y is selected from the group consisting of chlorine and fluorine.

5. The process of claim 4 wherein said fluoroalkyl, fluoro(alkoxyalkyl), perfluoroalkyl, and perfluoro(alkoxyalkyl) groups have from 1 to about 12 carbon atoms.

6. The process of claim 5 wherein said groups have from 1 to about 7 carbon atoms.

7. The process of claim 4 wherein X is selected from the group consisting of fluorine, chlorine, and perfluoromethyl.

8. The process of claim 1 wherein said α-halocarbonylfluoroalkanesulfonyl halides are selected from the class whose members fall within the representational general formula

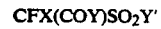

wherein X is selected from the group consisting of hydrogen; fluorine; chlorine; pentafluorosulfanyl; fluoroalkyl and fluoro(alkoxyalkyl) groups having from 1 to about 20 carbon atoms, containing no more than one atom of hydrogen or chlorine for every two carbon atoms, optionally containing carbon-carbon unsaturation, optionally being pentafluorosulfanyl-substituted, and optionally containing catenary nitrogen, oxygen, or sulfur; perfluoroalkyl and perfluoro(alkoxyalkyl) groups having from 1 to about 20 carbon atoms, optionally containing carbon-carbon unsaturation, optionally being pentafluorosulfanyl-substituted, and optionally containing catenary nitrogen, oxygen, or sulfur; and alkyl groups having from 1 to about 12 carbon atoms; and Y and Y' are selected from the group consisting of chlorine and fluorine, with the proviso that at least one of the groups Y and Y' is fluorine.

9. The process of claim 8 wherein said fluoroalkyl, fluoro(alkoxyalkyl), perfluoroalkyl, and perfluoro(alkoxyalkyl) groups have from 1 to about 12 carbon atoms.

10. The process of claim 9 wherein said groups have from 1 to about 7 carbon atoms.

11. The process of claim 8 wherein X is selected from the group consisting of fluorine, chlorine, and perfluoromethyl.

12. The process of claim 1 wherein said at least one precursor compound is selected from the group consisting of 1,1,2,2-tetrafluoroethane sultone, 1-(perfluoro-n-propyl)-1,2,2-trifluoroethane sultone, 1-(trifluoromethyl)-1,2,2-trifluoroethane sultone, a mixture of 2-chloro-1,1,2-trifluoroethane sultone and 1-chloro-1,2,2-trifluoroethane sultone, and a mixture of 1,1,2,2-tetrafluoroethane sultone and fluorocarbonyldifluoromethanesulfonyl fluoride.

13. A process for preparing perfluoromethanesulfonyl fluoride comprising electrochemically fluorinating in the presence of anhydrous hydrogen fluoride 1,1,2,2-tetrafluoroethane sultone or a mixture of 1,1,2,2-tetrafluoroethane sultone and fluorocarbonyldifluoromethanesulfonyl fluoride.

* * * * *

UNITED STATES PATENT AND TRADEMARK OFFICE
CERTIFICATE OF CORRECTION

PATENT NO. : 5,318,674                      Page 1 of 3
DATED : June 7, 1994
INVENTOR(S) : Fredrick E. Behr, Yuri Cheburkov, and John C. Hansen It is certified that error appears in the above-indentified patent and that said Letters Patent is hereby corrected as shown below:

Column 3, line 62   "England et al., supra," should read
                          --England et al., _supra_,--.

Column 3, line 63   "and Gard, supra," should read
                          --and Gard, _supra_,--.

Column 4, line 38   "below about 0° C." should read
                          --below about 0° C--.

Column 4, line 38   "to about 20° C." should read
                          --to about 20° C--.

Column 4, line 38   "high as about 50° C." should read
                          --high as about 50° C--.

Column 5, line 49   "supra) in a semi-continuous" should read
                          --_supra_) in a semi-continuous--.

Column 5, line 53   "C. and at a pressure" should read
                          --C and at a pressure--.

Column 5, line 54   "through a -40° C." should read
                          --through a -40° C--.

UNITED STATES PATENT AND TRADEMARK OFFICE
CERTIFICATE OF CORRECTION

PATENT NO. : 5,318,674

DATED : June 7, 1994

INVENTOR(S) : Fredrick E. Behr, Yuri Cheburkov, and John C. Hansen

It is certified that error appears in the above-indentified patent and that said Letters Patent is hereby corrected as shown below:

Column 6, line 18    "at 20° C." should read
                                  --at 20° C--.

Column 6, line 20    "C. condenser," should read
                                  --C condenser,--.

Column 6, line 39    "supra, page 6184)" should read
                                  --_supra_, page 6184)--.

Column 6, line 44    "C. and at atmospheric" should read
                                  --C and at atmospheric--.

Column 6, line 45    " -40° C. condenser," should read
                                  -- -40° C condenser,--.

Column 6, line 54    "$C_2F_5SO_2F$, (39%)," should read
                                  --$C_2F_5SO_2F$ (39%),--.

Column 6, line 68    "supra, page 6186)" should read
                                  --_supra_, page 6186)--.

Column 7, line 5    "at 30° C. and at" should read
                                  --at 30° C and at--.

Column 7, line 7    " -40° C. condenser," should read
                                  -- -40° C condenser,--.

UNITED STATES PATENT AND TRADEMARK OFFICE
CERTIFICATE OF CORRECTION

PATENT NO. : 5,318,674
DATED : June 7, 1994
INVENTOR(S) : Fredrick E. Behr, Yuri Cheburkov, and John C. Hansen It is certified that error appears in the above-indentified patent and that said Letters Patent is hereby corrected as shown below:

Column 7, line 40   "1g, boiling point 26°-28° C.)" should read
                        --1g, boiling point 26°-28° C)--.

Column 7, line 58   "C. condenser, whereby" should read
                        --C condenser, whereby--.

Column 7, line 63   " -40° C. condenser" should read
                        -- -40° C condenser--.

Signed and Sealed this

Thirtieth Day of April, 1996

Attest:

BRUCE LEHMAN

Attesting Officer                     Commissioner of Patents and Trademarks